United States Patent
Peters et al.

(10) Patent No.: US 7,160,899 B2
(45) Date of Patent: Jan. 9, 2007

(54) ADENOSINE $A_2A$ RECEPTOR ANTANGONISTS COMBINED WITH NEUROTROPHIC ACTIVITY COMPOUNDS IN THE TREATMENT OF PARKINSON'S DISEASE

(75) Inventors: Dan Peters, Malmö (SE); Lars Christian B. Rønn, Veksø (DK); Karin Sandager Nielsen, Fredensborg (DK)

(73) Assignee: Neurosearch A/S, Ballerup (DK)

( * ) Notice: Subject to any disclaimer, the term of this patent is extended or adjusted under 35 U.S.C. 154(b) by 342 days.

(21) Appl. No.: 10/473,809

(22) PCT Filed: Apr. 4, 2002

(86) PCT No.: PCT/DK02/00228

§ 371 (c)(1), (2), (4) Date: Oct. 2, 2003

(87) PCT Pub. No.: WO02/080957

PCT Pub. Date: Oct. 17, 2002

(65) Prior Publication Data

US 2004/0097540 A1 May 20, 2004

(30) Foreign Application Priority Data

Apr. 9, 2001 (DK) ................ 2001 00583

(51) Int. Cl.
*A61K 31/47* (2006.01)
(52) U.S. Cl. .............. 514/307; 514/2; 514/230.2; 514/237
(58) Field of Classification Search ............ None
See application file for complete search history.

(56) References Cited

U.S. PATENT DOCUMENTS

2001/0027196 A1  10/2001  Borroni et al.

FOREIGN PATENT DOCUMENTS

| DE | 43 25 254 A1 | 2/1994 |
| WO | WO 97/40035 | * 10/1997 |
| WO | WO 99/43678 A1 | 9/1999 |
| WO | WO 99/53909 A2 | 10/1999 |
| WO | WO 01/82946 A2 | 4/2001 |

OTHER PUBLICATIONS

Beers, M. H. and Berkow, R., Editors-in-chief, The Merck Manual of Diagnosis and Therapy, 17th Edition, pp. 1466-1473, 1999.*
Hess, Expert Opinion Ther. Patents, vol. 11, No. 10, pp. 1533-1561 (2001).
Lee et al., PNAS, vol. 98, No. 6, pp. 3555-3560 (2001).
Kiec-Kononowicz et al., Pure Appl. Chem., vol. 73, No. 9, pp. 1411-1420 (2001).
Ongini et al., Annals NY Academy of Sciences, pp. 30-49, 1997.
Heese et al., Neuroscience Letters, vol. 231, pp. 83-86 (1997).
Bennett, The Neuroscientist, vol. 7, No. 1, pp. 13-17 (2001).
Morelli et al., Drug Development Research, vol. 52, pp. 387-393 (2001).

* cited by examiner

*Primary Examiner*—Dwayne Jones
(74) *Attorney, Agent, or Firm*—Birch, Stewart, Kolasch & Birch, LLP

(57) ABSTRACT

This invention relates to the use of the combined action of a compound with neurotrophic activity and an adenosine $A_{2A}$ receptor antagonist for the treatment of Parkinson's disease.

6 Claims, No Drawings

ADENOSINE A₂A RECEPTOR ANTANGONISTS COMBINED WITH NEUROTROPHIC ACTIVITY COMPOUNDS IN THE TREATMENT OF PARKINSON'S DISEASE

This application is the national phase under 35 U.S.C. § 371 of PCT International Application No. PCT/DK02/00228 which has an International filing date of Apr. 4, 2002, which designated the United States of America.

TECHNICAL FIELD

This invention relates to the use of the combined action of a compound with neurotrophic activity and an adenosine $A_{2A}$ receptor antagonist for the treatment of Parkinson's disease.

BACKGROUND ART

Parkinson's disease is a neurodegenerative disease characterised by the progressive deterioration of motor skills, affecting about 4 million people worldwide. Parkinson's patients suffer from increasing difficulties in initiating movement, rigidity in arms and legs, as well as tremors. Although the specific cause of Parkinson's disease is unknown, it has been shown that the disease is associated with the degeneration of specific dopamine-containing neurons in a region of the brain known as the substantia nigra, which is believed to be involved in the coordination of movement.

One existing treatment is L-DOPA therapy, alone or combined with e.g. dopamine agonists. However, after three to five years of L-DOPA therapy, involuntary motor disturbances (dyskinesia) may appear.

Another treatment is the use of monoamine reuptake inhibitors (such as dopamine reuptake inhibitors) whereby the existing dopamine level in the synaptic cleft is increased.

A further possible therapy is the use of neurotrophic compounds which give a neuroregenerative effect on lesioned and damaged neurons.

A still further treatment suggested is the use of adenosine $A_{2A}$ receptor antagonists, which result in an enhanced dopaminergic activity. Furthermore, adenosine $A_{2A}$ receptors and their relation to neuroprotection have been discussed (Ongini, E. et al. (1997) Adenosine $A_{2A}$ receptors and neuroprotection, Ann NY Acad Sci 825:30–48).

There is a continued strong interest in the development of a more selective and effective therapy with fewer side effects for the treatment of patients with Parkinson's disease.

SUMMARY OF THE INVENTION

According to the invention it has now been found that the action of a compound with neurotrophic activity in combination with an adenosine $A_{2A}$ receptor antagonist advantageously can be used for the treatment of Parkinson's disease.

Accordingly, in its first aspect, the invention relates to a pharmaceutical composition comprising a therapeutically effective amount of at least one compound with neurotrophic activity and at least one adenosine $A_{2A}$ receptor antagonist, together with at least one pharmaceutically acceptable carrier or diluent.

In another aspect, the invention relates to the use of at least one compound with neurotrophic activity and at least one adenosine $A_{2A}$ receptor antagonist for the manufacture of a medicament for the treatment, prevention or alleviation of Parkinson's disease in a subject.

The principle combines a fast onset action (the effect of the adenosine $A_{2A}$ receptor antagonist) with a long-term effective principle (the neurotrophic activity). Thus, the adenosine $A_{2A}$ receptor antagonist relieves the symptoms of the disease (by increasing the dopaminergic activity), while the neurotrophic activity treats the cause of the disease (degenerating neurons) by slowing or even reversing the progression of the disease.

Other objects of the invention will be apparent to the person skilled in the art from the following detailed description and examples.

DETAILED DISCLOSURE OF THE INVENTION

In its first aspect, the invention provides the use of at least one compound with neurotrophic activity and at least one adenosine $A_{2A}$ receptor antagonist for the manufacture of a medicament for the treatment, prevention or alleviation of Parkinson's disease in a subject.

In a second aspect, the invention provides a pharmaceutical composition comprising a therapeutically effective amount of at least one compound with neurotrophic activity and at least one adenosine $A_{2A}$ receptor antagonist, together with at least one pharmaceutically acceptable carrier or diluent.

In a third aspect, the invention provides a combination of at least one compound with neurotrophic activity and at least one adenosine $A_{2A}$ receptor antagonist for use as a therapeutic agent.

In a further aspect, the invention provides a method of treatment, prevention or alleviation of Parkinson's disease in a subject, which method comprises administering to said subject a therapeutically effective combination of at least one compound with neurotrophic activity and at least one adenosine $A_{2A}$ receptor antagonist.

In a still further aspect, the invention provides a kit of parts comprising at least one compound with neurotrophic activity and at least one adenosine $A_{2A}$ receptor antagonist.

In one embodiment, the adenosine $A_{2A}$ antagonist is selected from the group consisting of KW-6002, ZM-241385, 8FB-PTP, SCH-58261, KF-17837, CGS-15943, DMPX and pharmaceutically acceptable salts thereof.

In a second embodiment, the compound with neurotrophic activity is a compound selected from the group consisting of 5-(4-Chlorophenyl)-8-methyl-6,7,8,9-tetrahydro-1-H-pyrrolo[3.2-h]isoquinoline-2,3-dione-3-oxime;

5-(4-Chlorophenyl)-6,7,8,9-tetrahydro-1-H-pyrrolo[3.2-h] naphthalene-2,3-dione-3-oxime;

GDNF;

Neublastin;

and pharmaceutically acceptable salts thereof.

In a special embodiment, the compound with neurotrophic activity is GDNF and the adenosine $A_{2A}$ antagonist is SCH-58261. In a further special embodiment, the compound with neurotrophic activity is GDNF and the adenosine $A_{2A}$ antagonist is KF-17837.

In a further embodiment, the pharmaceutical composition as described above is for use in the treatment, prevention or alleviation of a neurodegenerative condition. In a still further embodiment, the pharmaceutical composition as described above is for use in the treatment, prevention or alleviation of Parkinson's disease in a subject.

The subject to be treated according to this invention is a living body, preferably a mammal, most preferably a human, in need for such treatment.

Any possible combination of two or more of the embodiments described herein is comprised within the scope of the present invention.

Compounds With Neurotrophic Activity

Endogenous neurotrophic factors, such as nerve growth factor (NGF), brain-derived neurotrophic factor (BDNF), epidermal growth factor (EGF), basic fibroblast growth factor (bFGF, or FGF2), NT¾, neurturin (NTN), neublastin/ artemin, persephin, and glial cell-line derived neurotrophic factor (GDNF), promote the differentiation, growth and survival of numerous peripheral and central nervous system neurons during development and adulthood.

In the context of this invention, compounds with neurotrophic activity are compounds that mimic or enhance the function of one or more endogenous neurotrophic factors. In one embodiment, a compound with neurotrophic activity is a compound that mimics or enhances the function of NGF, BDNF, and/or GDNF. In a further embodiment, a compound with neurotrophic activity is a compound that mimics or enhances the function of bFGF and/or EGF. In a special embodiment, a compound with neurotrophic activity is a compound that mimics or enhances the function of NGF. The neurotrophic activity has not been ascribed to a specific step in the interaction between the growth factor and its receptor or in the growth factor signal transduction pathway.

The potential of a given substance to act as a compound with neurotrophic activity may be determined using standard in vitro binding assays and/or standard in vivo functional tests, such as those described in "Test methods".

In one embodiment, the compound with neurotrophic activity at 1 µM shows more than 10% (more preferably more than 20%, and most preferably more than 30%) of the effect of 3 nM NGF when tested in the PC12 cells survival assay (method 2).

In a second embodiment, the compound with neurotrophic activity at 1 µM shows more than 10% (more preferably more than 20%, and most preferably more than 30%) of the effect of 10 ng/ml GDNF when testing the survival of embryonic rat dopaminergic neurons (method 3).

In a special embodiment, the compound with neurotrophic activity is not an adenosine $A_{2A}$ receptor antagonist.

In a further embodiment, the compound with neurotrophic activity and the adenosine $A_{2A}$ receptor antagonist are not the same compound.

Compounds with neurotrophic activities for use according to the invention include those substances described in the patent applications WO 98/07705 (Takeda Chem Ind Ltd), WO 00/34262 (Takeda Chem Ind Ltd), WO 00/32197 (Alcon Lab Inc), WO 97/40035 (NeuroSearch), WO 00/43397 (NeuroSearch), international application PCT/DK01/00049 (NeuroSearch), JP 2000226388-A (Takeda Chem Ind Ltd), WO 00/32197 (Alcon Lab), and WO 00/46222 (Schering AG).

Further examples of compounds with neurotrophic activity according to the invention include 1-(1,3-benzodioxol-5-yl)-7,8,9,10-tetrahydro-1,3-benzodioxol[4,5-g]isoquinolin-7-one (Takeda), 2-(2,2,4,6,7-Pentamethyl-3-phenyl-2,3-dihydro-1-benzofuran-5-yl)-isoindoline (Takeda), 4-Aryl-1-phenylalkyl-1,2,3,6-tetrahydropyridine (Sanofi-Synthelabo), SR-57746A or 1-(2-napht-2-yl)ethyl-4-(3-trifluoromethylphenyl)-1,2,5,6-tetrahydropyridine (Sanofi-Synthelabo), AIT-082 (NeoTherapeutics), NIL-A (Amgen Inc), K-252a (Cephalon), CEP-1347, GPI-1046 (Guilford), CTQ3, CTQ5 and CTQ8 (Centre de Neurochimie du CNRS), V-10,367 and V-13,661 (Vertex Pharmaceuticals Inc), ABS-205 (American Biogenic Sciences), Dexanabinol or HU-211 (Pharmos), or salts, free bases, racemates or enantiomers thereof.

The above examples of compounds with neurotrophic activity are not intended to be in any way limiting to the scope of the invention as claimed.

Adenosine $A_{2A}$ Receptor Antagonists

In the context of the present invention, adenosine $A_{2A}$ receptor antagonists include xanthine based analogs and non-xanthine based analogs.

Examples of adenosine $A_{2A}$ receptor antagonists include KW-6002 (Kyowa Hakko Kogyo Co Ltd), ZM-241385, 8FB-PTP, SCH-58261,-KF-17837, CGS-15943, DMPX, 8-(m-chlorostyryl)-DMPX, 8-(m-bromostyryl)-DMPX (or BS-DMPX), 8-(3,4-dimethoxystyryl)-DMPX.

The potential of a given substance to act as an adenosine $A_{2A}$ receptor antagonists may be determined using standard in vitro binding assays and/or standard in vivo functionality tests, such as those described in "Test methods".

In one embodiment, the adenosine $A_{2A}$ receptor antagonists show an $IC_{50}$ value of less than 10 µM, preferably less than 1 µM, and most preferably less than 0.1 µM, when tested for In vitro inhibition of $^3$H-ZM 241385 binding (test method 7a).

The above examples of adenosine $A_{2A}$ receptor antagonists are not intended to be in any way limiting to the scope of the invention as claimed.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining an active compound for use according to the invention and its pharmaceutically acceptable acid addition salt.

Metal salts of an active compound for use according to the invention includes alkali metal salts, such as the sodium salt of an active compound for use according to the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The active compounds for use according to the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Pharmaceutical Compositions

While the active compounds for use according to the invention in therapy may be administered in the form of the raw chemical compounds, it is preferred to introduce the active ingredient, optionally in the form of physiologically acceptable salts, in a pharmaceutical composition together with one or more adjuvants, excipients, carriers, buffers, diluents, and/or other customary pharmaceutical auxiliaries.

The active compounds for use according to the invention may be administered separately or in combination. Thus the pharmaceutical compositions for use according to the invention may comprise the active compounds for use separately or in combination.

In one embodiment, the invention provides pharmaceutical compositions comprising the active compounds of the invention, or pharmaceutically acceptable salts or derivative thereof, together with one or more pharmaceutically acceptable carriers, and, optionally, other therapeutic and/or prophylactic ingredients, know and used in the art. The carrier (s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The active compounds of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The active compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from an active compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The active compounds for use according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the active compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The pharmaceutical composition of the invention preferably is for use in the treatment, prevention or alleviation of Parkinson's disease in a subject.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.01 to about 500 mg of active ingredient per individual dose, preferably of from about 0.1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

The pharmaceutical composition according to invention may include or may be used or administered in combination with one or more additional drugs useful for the treatment, prevention or alleviation of Parkinson's disease. Such additional drugs include L-DODA (optionally in combination with decarboxylase inhibitors (such as carbidopa) or COMT inhibitors (such as entacapone)), monoamine oxidase inhibitors, monoamine oxidase B inhibitors (such as selegiline), dopamine agonists (such as bromocriptine, pergolide, cabergoline, ropinirole, pramipexole, or apomorphine in combination with domperidone), monoamine reuptake inhibitors (such as those described in WO 97/16451 (NeuroSearch) and WO 97/13770 (NeuroSearch), or ALE-26018), dopamine reuptake inhibitors (such as those described in the patents U.S. Pat. No. 6,011,070, U.S. Pat. No. 5,821,386, U.S. Pat. No. 6,001,330, U.S. Pat. No. 5,795,915, U.S. Pat. No. 5,574,060), NA/DA-uptake inhibitors (such as Venlafaxin, Minacipram, Reboxetin), classic tricyclic antidepressiva (such as Imipramin, Amitriptyline, Clomipramine, Doxepin, Amoxapine, Desipramine, Maprotiline, Nortriptyline and Protriptyline), selective dopamine reuptake inhibitors (such as GRB-12909, GRB-12935, Indatraline (Lu-19-005), Bupropion, Amfonelic acid, BTCP, Mazindol, Nomifensine, Beta-CFT (WIN 35,428), Beta-CTP (WIN 35,065-2), Beta-CIT (RTI-55), GYKI 52895, 4',4"-Diflouro-3-alpha-diphenyl-methoxytropane, 4'-Chloro-3-alpha-diphenylmethoxytropane, 5-(4-Chlorophenyl)-8-methyl-6,7,8,9-tetrahydro-1-H-pyrrolo[3.2-h]isoquinoline-2,3-dione-3-oxime; and 5-(4-Chlorphenyl)-6,7,8,9-tetrahydro-1-H-pyrrolo[3.2-h]naphthalene-2,3-dione-3-oxime), or relatively selective dopamine reuptake inhibitors (such as amineptine, 3,4-dichlorophenyl 4-(3,4-dichlorophenyl)-4-hydroxy-1-methyl-3-piperidyl ketone (Wang, S et al, 1999), 1-[2-(diphenylmethoxy)ethyl]-4-(3-phenylpropyl)-homopiperazine, (LR-1111),1-[2-(diphenylmethoxy)-ethyl]4-(3-phenyl-2-propenyl)-homopiperazine, (S)-(–)-1-[2(diphenylmethoxy)ethyl]-2-[[N-(3-phenylpropyl)amino]methyl]pyrrolidine, and (S)-(–)-1-[2-[bis(4-fluorophenyl)-methoxy]ethyl]-2-[[N-(3-phenylpropyl)amino]methyl] pyrrolidine).

Furthermore, the treatment of the invention may be combined with other known treatments of Parkinson's disease, such as grafting of dopamine-secreting cells into the striatum or application of neurotrophic growth factors into the lateral ventricle.

The invention is further illustrated with reference to the following test methods and examples which are not intended to be in any way limiting to the scope of the invention as claimed.

Test Methods

Method 1

Stimulation of Neurite Outgrowth in PC12 Cells

In this test, the ability of a compound with neurotrophic activity (below the compound) to potentiate NGF-induced neurite outgrowth in PC12 cells is assessed.

Method

PC12 cells are seeded in tissue culture plates coated with collagen at a cell density of 15,000/cm² in DMEM with 7.5% FCS and 7.5% DHS. Next day the medium is changed to medium supplemented with the compound in the absence or presence of NGF.

Two days after the medium change, cells are fixed in 4% paraformaldehyde and stained for neurofilament. Cells are fixed by in tissue culture plates by incubation in 4% paraformaldehyde in PBS, followed by permeabilization in 0.05% Triton-X100 in the presence of 10% DHS to block non-specific binding sites. After washing, the plates are incubated with anti-neurofilament (NF) antibody (clone RT97, Boehringer) diluted 1:200 in 0.05% Triton-X100/10% DHS followed by incubation with biotinylated anti-mouse immunoglobulin RPN1001 (Amersham) diluted 1:200. NF-immunoreactive cells are stained using the ABC-complexHRP kit K0355 (DAKO) and 3,3-diaminobenzidine tetrahydrochloride (DAB) as substrate.

Estimation of total cell number per well, as well as the total neurite length are done using unbiased 2D stereology (CAST-grid system connected to a Olympus BH-2 microscope).

Method 2

PC12 Cells Survival Assay

In this test, the effect of a compound with neurotrophic activity (below: the compound) on the survival of PC12 cells is assessed.

Method

PC12 cells are seeded in collagen-coated 96 well plates in growth medium supplemented with 2 nM mouse 7S NGF (Alomone Labs Ltd., Jerusalem, Israel) and cultured for 6 days. The medium is then changed to serum-free DMEM supplemented with the compound. NGF (3 nM) is included as a positive control. After 4 days of incubation, cell viability is evaluated by using the CyQUANT Cell Proliferation assay according to the manufacturer's instructions (Molecular Probes, C-7026). Briefly, medium is aspirated, and cells are incubated at –80° C. for at least 1 hour. Cells are then thawed and incubated in a buffer containing the fluorescent CyQUANT dye, which exhibits strong fluorescence enhancement when bound to nucleic acids. Fluorescence measured with excitation at 480 nm and emission detection af 520 nm can be correlated to the number of living cells in the wells.

Method 3

Survival of Embryonic Rat Dopaminergic Neurons

In this test, the effect of a compound with neurotrophic activity (below: the compound) on the survival of dopaminergic neurons in dissociated cultures established from rat E14 ventral mesencephali (VM) is assessed.

Method

Embryonic rat brains (Wistar; E14) are isolated under sterile conditions placed in chilled Gey's balanced salt solution (GIBCO) with glucose (6.5 mg/ml).

The ventral mesencephali are dissected out, cut into small tissue pieces, placed in Neurobasal medium with B27 supplement and gently pressed through a 80 µm Nitex filter. The cells are counted using a hemocytometer and plated in a 6 well multi-dish at a density of approximately $2.0 \times 10^6$ cells/well. Culture dishes are pre-coated with poly-D-lysine.

After 1 hour, the medium is removed and fresh medium added with or without the compound to be tested (1.5 ml/well). (untreated cultures serve as controls). The medium is changed every other day and antimitotics and antibiotics are not used at any stage.

After 7 days in culture, cultures are immunostained for tyrosine hydroxylase (TH). Briefly, the cells are washed in 0.05M tris-buffered saline (TBS, pH 7.4) containing 1% Triton X-100 for 3×15 minutes and incubated with 10% foetal bovine serum (FBS, Life Technologies) in TBS for 30 minutes. The cells are then incubated for 24 hours at 4° C. with monoclonal mouse anti-TH antibody (Boehringer Mannheim) diluted 1:600 in TBS with 10% FBS. After rinsing in TBS with 1% Triton X-100 for 3×15 minutes, cells are incubated for 60 minutes with biotinylated anti-mouse IgG antibody (Amersham) diluted 1:200 in TBS with 10% FBS. The cells are then washed in TBS with 1% Triton X-100 (3×15 minutes) and incubated for 60 minutes with strepta-vidine-peroxidase (Dako) diluted 1:200 in TBS with 10% FBS. After washing in TBS (3×15 minutes), bound antibody is visualised by treatment with 0.05% 3,3-diaminobenzidine (Sigma) in TBS containing 0.01% $H_2O_2$. TH-immunoreactive (ir) cells are counted manually.

Method 4

Survival of Dopaminergic Neurons from E28 Pig Ventral Mesencephali

In this test, the effect of a compound with neurotrophic activity (below: the compound) on the survival of dopaminergic neurons in organotypic slice cultures established from pig E28 ventral mesencephali is assessed.

Method

Ventral mesencephali (VM) are isolated from porcine embryos (E28) under sterile conditions, chopped into 400 µm slices and placed in chilled Gey's balanced salt solution (GIBCO) with glucose (6.5 mg/ml). The tissue slices are cultured by the interface culture method, originally developed by Stoppini et al. [L. Stoppini, P. A. Buchs, D. Muller: A simple method for organotypic cultures of nervous tissue; *J. Neurosci. Methods* 1991 37 173–182].

In brief, slices are placed on semiporous membranes (Millipore, 0.3 µm; 4 slices/membrane) placed as inserts in 6-well plates (Costar) with serum containing medium (Gibco BRL). Each well contained 1 ml medium (50% Optimem, 25% horse serum, 25% Hank's balanced salt solution (all GIBCO)) supplemented with D-glucose to a final concentration of 25 mM.

At day 3, the medium is replaced by defined serum-free medium (Neurobasal medium with B27 supplement, Life Technologies). The cultures are grown in an incubator with 5% $CO_2$ at 36° C. for 21 days after which the sections are immunostained for TH as described in Test 2. One group of slice cultures are treated chronically with the compound at a concentration of 1 µM. Untreated cultures serves as controls. The medium is changed twice a week and antimitotics and antibiotics are not used at any stage.

Quantification of TH-ir neurons is performed on coded slides (to allow analysis by experiments "blinded" to sample identity) using an Olympus C.A.S.T. Grid system (version 1.10; Olympus, Albertslund, Denmark) composed of an Olympus BX50 microscope and a computer controlled x-y-z step motor stage. The area of the culture slice is delineated and a counting frame is randomly placed to mark the first area to be sampled. The frame is then systematically moved through the sections and the TH-ir cells counted.

Method 5

Potentiation of NGF Signal Transduction in PC12 Cells

In this test the effect of a compound with neurotrophic activity (below: the compound) on NGF-induced phosphorylation of the ERKs and the Akt kinase is assessed.

Method

Approximately 200,000 PC12 cells are plated in a 24 well plate in DMEM with 7.5% FCS and 7.5% DHS and incubated ON. The next day NGF and the compound are added to the cells and they are incubated for 24 hours after which the cells are harvested in 2× Laemmli sample buffer.

Total cell lysate is electrophoresed on 8–18% gradient SDS gels which are electroblotted to PVDF membranes. Phosphorylated ERK1 and ERK2 are immunodetected by using mouse anti-Phospho-p44/p42 MAP kinase E10 mAb (New England Biolabs #9106) and HRP-linked anti-mouse antibody. Phosphorylated Akt kinase is immunodetected by using rabbit phospho-specific Akt (Ser473) antibody (New England Biolabs #9271) and HRP-linked anti-rabbit antibody. Bands are detected by chemiluminescence using the ECL system (Amersham).

Method 6

Stimulation of CREB Phosphorylation in Undifferentiated PC12 Cells

In this method the effect of a compound with neurotrophic activity (below: the compound) on CREB (cyclic AMP-responsive element binding protein) phosphorylation is assessed.

Method

Approximately $7.5 \times 10^5$ PC12 cells per well are plated in collagen coated 6-well plates in DMEM with 0.75% FCS and 0.75% DHS and incubated for 48 hours. Cells are then further starved for 2 hours in serum free DMEM before stimulation with the indicated compounds for 5, 10 or 20 minutes. Cells are harvested in 1× heated sample buffer (2% SDS, 400 mM Tris, pH 8.0, 10 mM DTT and 0.25 mM $Na_3VO_4$) and the cell lysates are electrophoresed on 8–18% gradient SDS gels, which are electroblotted to PVDF membranes.

Phosphorylated CREB is immunodetected by using rabbit anti-Phospho-CREB (Upstate Biotechnology #06-519) followed by HRP-linked anti-rabbit antibody (Amersham Life Science #NA 934). Bands are detected by chemiluminescence using the ECL system (Amersham).

Method 7a

In Vitro Inhibition of $^3$H-ZM 241385 Binding

In this method the ability of an adenosine $A_{2A}$ receptor antagonist to inhibit the specific binding of the selective and potent adenosine $A_{2A}$ receptor antagonist $^3$H-ZM 241385 in striatal tissue is assessed.

Tissue Preparation

Preparations are performed at 0–4° C. unless otherwise indicated. Striatal tissue from male Wistar rats (150–250 g) is homogenised using an Ultra-Turrax homogeniser for 10–20 sec in 20 vol. of Tris, HCl (50 mM, pH 7.4). This membrane homogenate is then centrifuged at 48,000×g for 10 min. The supernatant is discarded and the pellet is resuspended in buffer containing 2 IU/ml of adenosine deaminase to 10 mg/ml of original tissue weight and incubated at 37° C. for 30 min to remove endogenous adenosine. This membrane homogenate is recentrifuged and the final pellet is resuspended in 50 vol. of buffer and frozen at −80° C. until the time of assay.

Assay

The membrane preparation is thawed and centrifuged at 2° C. for 10 min at 27,000×g, and the pellet is resuspended in 50 mM Tris, HCl, pH 7.4, containing 10 mM $MgCl_2$ (500 ml buffer per g of original tissue), and then used for binding assays. Aliquots of 0.5 ml homogenate are added to 0.025 ml of test solution and 0.025 ml of $^3$H-ZM 241385 (1 nM, final concentration), mixed and incubated for 30 min at room temperature. Non-specific binding is determined using NECA (100 µM, final concentration). After incubation the samples are poured directly onto Whatman GF/C glass fibre filters under suction and immediately washed with 2×5 ml ice-cold buffer. The amount of radioactivity on the filters is determined by conventional liquid scintillation counting. Specific binding is total binding minus non-specific binding.

Results

The test value is given as an $IC_{50}$ (the concentration (µM) of the test substance which inhibits the specific binding of $^3$H-ZM 241385 by 50%).

Method 7b

In Vitro Inhibition of $^3$H-CGS 21680 Binding

In this method the ability of an adenosine $A_{2A}$ receptor antagonist to inhibit the specific binding of the adenosine $A_{2A}$ agonist $^3$H-CGS 21680 in striatal tissue is assessed.

Tissue Preparation

As described in method 7a above.

Assay

The membrane preparation is thawed and centrifuged at 2° C. for 10 min at 27,000×g, and the pellet is resuspended in 50 mM Tris, HCl, pH 7.4, containing 10 mM $MgCl_2$ (200 ml buffer per g of original tissue), and then used for binding assays. Aliquots of 0.5 ml homogenate are added to 0.025 ml of test solution and 0.0250 ml of $^3$H-CGS 21680 (5 nM, final concentration), mixed and incubated for 2 hr at room temperature. Non-specific binding is determined using NECA (100 µM, final concentration). After incubation the samples are poured directly onto Whatman GF/C glass fibre filters under suction and immediately washed with 2×5 ml ice-cold buffer. The amount of radioactivity on the filters is determined by conventional liquid scintillation counting. Specific binding is total binding minus non-specific binding.

Results

The test value is given as an $IC_{50}$ (the concentration (μM) of the test substance which inhibits the specific binding of $^3$H-CGS 21680 by 50%).

The $IC_{50}$ values of method 7a and 7b are determined from the inhibition curve. If a full curve is not available a 25–75% inhibition of specific binding must be obtained, before calculation of an $IC_{50}$.

$$IC_{50} = \text{(applied test substance concentration, μM)} \times \frac{1}{\left(\frac{C_o}{C_x} - 1\right)}$$

where $C_o$ is specific binding in control assays and $C_x$ is the specific binding in the test assay. (The calculations assume normal mass-action kinetics).

Method 8

Effect of a Compound on Extracellular Dopamine Measured by Microdialysis

In this test, the ability of a compound with neurotrophic activity to increase dopamine in various brain regions is assessed.

Male SPF Mol Wistar rats weighing 300–350 g are obtained from Møllegaard Breeding and Research Centre and housed in standard Macrolon cages sized 24×36×18 cm for at least 5 days under standard conditions at a temperature of 23±2° C. and a humidity of 60%±10%, and a 12 h light and dark cycle. The rats are housed in groups of two with food and water freely available ad libitum. For microdialysis, the rat is placed in a stereotaxic instrument under halothane anesthesia using 1½% halothane, 20% oxygen and 80% nitrous oxide. The rectal temperature is monitored and maintained at 37.0±1° C. during the experimental period using a heating pad (CMA 150 Carnegie Medicin). A small hole is drilled to allow a vertical probe (CMA/123), to be stereotaxically implanted into the right striatum, using the following coordinates relative to bregma: AP +1 mm; L 3 mm; DV −6 mm. The probes for the nucleus accumbens (CMA 122) is implanted vertical at the following coordinates: AP +2.4, L 1.4 and DV −8 mm. Similar experiments are performed with probes implanted into the nucleus accumbens in non anaesthetised freely moving animals. These experiments are performed 48 h after surgery during the daylight period in animals housed individually in plastic cages with food and water available ad libitum. In all cases, the injection sites are confirmed histologically according to the atlas of Paxinos and Watson.

After an initial 2 h period, samples of dialysate are collected from halothane anaesthetised rats. The dosing of a test compound to these rats are usually initiated after the collection of 3 base line analyses. Dopamine and its metabolites are rapidly frozen to −18° C. and then analyzed as soon as possible thereafter. The dialysis probe is perfused at a rate of 2 μl/min (by a CMA/100 microperfusion pump) with Ringer's solution (147 mM NaCl, 4 mM KCl, 2.3 mM CaCl) i.e. Ringer's solution (NaCl 4.3 g, KCl 150 mg, $CaCl_2$ 110.3 mg ad 500 ml) adjusted to pH 6.5 with 2 mM sodium phosphate buffer. The Ringer solution is filtered before use through Millipore glass filters (0.22 μm). The dialysate fractions (40 μl) are collected at 20 min intervals and then injected into the HPLC system. The concentration of dopamine (DA), dihydroxy phenyl acetic acid (DOPAC), homovanillic acid (HVA) and 5-hydroxy indolacetic acid (5-HIM) are determined by high-performance liquid chromatography with electrochemical detection (HPLC-ED). The column is a reverse-phase liquid chromatography Catecholamine 3 μm ESA column at 23° C., the mobile phase consisting of 0.055 M sodium acetate with 0.1 nM octanesulfonic acid, 0.01 mM Na EDTA, and 10% methanol pH 3.7 adjusted with glacial acetic acid). The mobil phase is delivered by a HPLC pump (ESA) at 0.55 ml/min. Electrochemical detection is accomplished using an amperometric detector (Antec) with a glassy carbon electrode (0.8 V an Ag/AgCl reference) or a coloumetric detector (Choulochem II model ESA; with a high sensitivity analytical cell (5011). (0,4V an Ag/AgCl reference). Chromatograrns are recorded by an integrator. The data are calculated as percent change of the basal concentration, the 100% value being defined as the average of the last 3 pretreatment values for each rat. The mean percentage values are then calculated for each 20 min sample for the rats in each group of treatment.

Method 9

Effect of a Compound on Degeneration of Nigral Dopaminergic Neurons After a 6-OHDA Lesion of the Medial Forebrain Bundle and the Ventral Tegmental Area In this test, the ability of a compound with neurotrophic activity to increase the number of surviving dopamine neurons in the substantia nigra after a striatal 6-OHDA lesion is assessed.

FluoroGold (0.2% solution in 0.9% NaCl, 0.2 μl/side) is injected bilaterally in the striatum of halothane anaesthetised female Sprague Dawiey rats weighing approximately 200–250 g with a 10 μl Hamilton syringe. The following coordinates are used: AP=+1.0 mm, ML=+/−3.0 mm, DV=−5.0 mm, tooth bar=0.0. After 1 week, 6-OHDA (20 μg free base dissolved in 0.9% NaCl supplemented with 0.02% ascorbic acid) is injected unilaterally in the medial forebrain bundle (MFB) and the ventral tegmental area (VTA) with a glass capillary using the following coordinates: AP=−4.4 mm, ML=−1.2 mm, DV=−7.8 mm, tooth bar=−2.3 (MFB) and AP=−4.0 mm, ML=−0.8.mm, DV=−8.0 mm, tooth bar=+3.4 (VTA).

Test compound or vehicle is administered i.p., p.o., s.c. or i.v. either daily or at specified time points starting after the 6-OHDA injection. Three to four weeks after the 6-OHDA injection, the rats are deeply anaesthetised and transcardially perfused with 0.9% NaCl for 1 min followed by 4% paraformaldehyde in 0.1 M phosphate buffer for 6 min. Brains are dissected out and postfixed for three to six hours in formalin and then transferred to 25% sucrose in 0.1 M phosphate buffer for 48 hours. Series of 40 μm sections are obtained by freezing microtomy through the striatum and the substantia nigra. Sections are stained for tyrosine hydroxylase (TH). Surviving dopaminergic neurons in the 6-OHDA lesioned and intact sides are quantified blindly by stereologically counting the number of retrogradely labelled neurons in the substantia nigra displaying fluorogold fluorescence and by counting the number of neurons displaying TH immunoreactivity.

Method 10

Effect of a Compound on Turning Behaviour After 6-OHDA Lesion

In this test, the ability of an adenosine $A_{2A}$ receptor antagonist and/or a compound with neurotrophic activity to influence the turning behaviour after a striatal or medial forebrain bundle and ventral tegmental area 6-OHDA lesion is assessed.

6-OHDA (20 μg free base dissolved in 0.9% NaCl supplemented with 0.02% ascorbic acid) is injected unilaterally in the striatum or in the medial forebrain bundle and the ventral tegmental area of halothane anaesthetised female Sprague Dawley rats weighing approximately 200–250 g with a glass capillary. Test compound or vehicle is administered i.p., p.o., s.c. or i.v. either daily or at specified time points starting after the 6-OHDA injection.

At different time points after the 6-OHDA injection, the rotational behaviour of the 6-OHDA lesioned animals after administration of amphetamine (2.5 mg/kg i.p.), apomorphine (0.25 mg/kg s.c.), or L-dopa (2–10 mg/kg i.p.) is monitored in automated rotometer bowls.

Method 11

Effect of a Compound on Catalepsy

In this test, the ability of an adenosine $A_{2A}$ receptor antagonist and/or a compound with neurotrophic activity to influence catalepsy induced by haloperidol is assessed.

Male wistar rats weighing 200–250 g are housed in cages of four rats with food and water ad lib and with a 12 hour light cucle. Test compound or vehicle is administered i.p., p.o., s.c. or i.v. at specified time points before haloperidole administration (0.1 mg/kg s.c.). For each dose levels 6 rats are tested. Testing for catalepsy is performed at 15 min intervals including 4 tests performed consecutively, in each test evaluating the intensity of catalepsy for 10 sec.
1) A vertical wire netting (40×40 cm high). The meshes (openings) of the netting are approximately 1×2 cm.
2) A horizontal bar 9 cm above the floor
3) A 9 cm high block (bar)
4) A 3 cm high block (cork)

The rat is placed in the middle of the vertical wire netting, then on the horizontal bar in an extended position supporting the forelegs on the bar. The intensity of catalepsy is evaluated according to a criterion of 10 sec of total immobility for a score of 2. Minor movements of the head or the body give the score of 1 and a score of 0 is given, if the rat shows no syndrome. The rats are then tested after the bar test, whether or not they were willing to sit with the left or right foreleg placed first on the 9 and then on the 3 cm block for a duration of 10 sec. The maximum score for all 4 tests is thus a total of 8.

Method 12

Effect of the Separate or Combined Administration of an Adenosine Receptor $A_{2A}$ Antagonist and a Compound with Neurotrophic Activity on Striatal Dopamine in Mice Treated with MPTP In this test, the ability of the separate or combined administration of an adenosine $A_{2A}$ receptor antagonist and a compound with neurotrophic activity to increase striatal dopamine in mice treated with MPTP is assessed.

Female C57Bl/6J mice weighing 20–25 grams (M&E breeding centre, Ltd. Ejby, Denmark) are adapted to the laboratory for 5–7 days before the experiments with food and water freely available, room temperature 22–24° C. Light is on/off at 7 am and 6 pm respectively. At least 5–8 mice are used per group. MPTP (RBI) is dissolved in saline just before the experiments and is tested in various doses. The effect of the separate administration of the adenosine $A_{2A}$ receptor antagonist is examined after daily administration of the compound in various doses s.c., p.o., i.p. or i.c.v. 1–5 days prior to MPTP treatment. The mice are sacrificed 48 hr after the MPTP treatment. The effect of the separate administration of the neurotrophic compound is examined after daily administration of the compound in various doses s.c., p.o., i.p. or i.c.v. 1–5 days succeeding MPTP treatment. The mice are sacrificed 48 hr after the last treatment with the neurotrophic compound. The effect of the combined administration of the two compounds are examined by administering the adenosine $A_{2A}$ receptor antagonist daily in various doses s.c., p.o., i.p. or i.c.v for 1–5 days prior to MPTP treatment and in the same animals, administering the neurotrophic compound daily in various doses s.c., p.o., i.p. or i.c.v. for 1–5 days post MPTP treatment. The mice are sacrificed 48 hr after the last treatment with the neurotrophic compound. The brains are rapidly removed and the striatum of the mice are dissected, frozen and stored at −80° C. until biochemical analysis of dopamine and its metabolites HVA and DOPAC. On the day of analysis, one striatum per mouse (weighing 5–7 mg) is homogenised in 1 ml of 0.1N perchloric acid containing 5% EDTA. After centrifugation 14,000×G for 30 min. 200 μL of the supernatant is filtered through a glass 0.22 μm filter. 20 μL is then injected into the ESA Coulochem II HPLC equipment with the following column (Catecholamine HR-80 4.6 mm×80 mm 3 μm Nucleosil C 18). The eluent is 10.25 g $NaH_2PO_4$, 185 mg EDTA, 100 mg octansulphonic acid, 9% methanol, pH 3.7, add 500 ml MilliQ water, filtered through 0.22 μm filter. The Colochem ESA analytical cell is 5014A and the ESA detector has the following settings: E2–175 mV, run time 16 min. for the elution of dopamine, DOPAC and HVA (DOPAC: 4.3 min; dopamine=6.4 min and HVA=12.7 min). The autoinjector SHIMADZY sil-10A has the following settings: injection vol. 20 μL, 16min. analysis, temp. 4° C. Flow rate from the pump is 0.80 ml/min. The analyses are calibrated with standards of 3 pM of dopamine, HVA and DOPAC for each 12-analysis run and are compared with the standard curves.

Method 13

Effect of the Separate or Combined Administration of an Adenosine Receptor $A_{2A}$ Antagonist and a Compound with Neurotrphic Activity on Degeneration of Nigral Dopaminergic Neurons After Striatal 6-OHDA Lesion In this test, the ability of the separate or combined administration of an adenosine $A_{2A}$ receptor antagonist and a compound with neurotrophic activity to increase the number of surviving dopamine neurons in the substantia nigra after a striatal 6-OHDA lesion is assessed. FluorGold (0.2% solution in 0.9% NaCl, 0.2 μL/side) is injected bilaterally in the striatum of halothane anaesthetised female Sprague Dawley or Wistar rats weighing approximately 200–250 grams with a 10 μL Hamilton syringe. The following coordinates are used: AP: +1.0 mm, ML=+/−3.0 mm, DV=−5.0 mm, tooth bar=0.0 mm. After 1 week, 6-OHDA (20 μg free base dissolved in 0.9% NaCl supplemented with 0.02% ascorbic acid) is injected unilaterally in the striatum with a glass capillary using the following coordinates: APO+1.0 mm, ML=−3.0 mm, DV=−5.0 mm, tooth bar=0.0 mm. The effect of separate administration of the adenosine $A_{2A}$ receptor antagonist is examined after administration of the compound in various doses s.c., p.o., i.p. or i.c.v. either daily or at specified time points prior to the 6-OHDA injection. The effect of separate administration of the neurotrophic compound is examined after administration of the compound in various doses s.c., p.o., i.p. or i.c.v. either daily or at specified time points after the 6-OHDA injection. The effect of the combined administration of the two compounds are examined by administering the adenosine $A_{2A}$ receptor antagonist daily or at specified time points in various doses s.c., p.o., i.p. or i.c.v prior to the 6-OHDA injection, and in the same animals, administering the neuro-trophic compound daily or at specified time points in various doses s.c., p.o., i.p. or i.c.v. after the 6-OHDA lesion. Three to four weeks after the 6-OHDA injectio, the rats are deeply anaesthetised and transcardially perfused with 0.9% NaCl for 1 min. followed by 4% paraformaldehyde in 0.1M phosphate buffer for 6 min.

Brains are dissected out and postfixed for three to six hours in formalin and then transferred to 25% sucrose in 0.1 M phosphate buffer for 48 hours. Series of 40 μm sections are obtained by freezing microtomy through the striatum and the substanba nigra. Sections are stained for tyrosine hydroxylase (TH) immuno activity using mouse-anti-TH (Chemicon, #MAB 318). Sections are rinsed in KPBS and thereafter quenched using 10% methanol+3% hydrogenperoxide in KPBS. Preincubation for one hour in 2% normal horse serum (NHS)+0.3% Triton X-100 in KPBS. Thereafter, sections are incubated inmouse-anti-TH (Chemicon, #MAB 318) 1:2000+2% NHS+0.3% Triton X-100 in KPBS over night. After rinsing in KPBS, sections are incubated in biotinylated horse-anti-mouse (Vector) 1:200 in 0.3% Triton in KPBS for 2 hours. After rinsing in KPBS, immunoreativity is visualised by the ABC reaction (Vector Kit) followed by DAB staining. Surviving dopaminergic neurons in the 6-OHDA lesioned and intact sides are quantified blindly by stereologically counting the number of retrogradely labelled neurons in the substantia nigra displaying fluorogold fluorescence and by counting the number of neurons displaying TH immunoreactivity. In some cases, the-degree of neuronal survival is estimated by assigning a score from one to five to each section depending on the fraction of surviving dopaminergic cells as estimated blindly by observing sections processed for fluorogold flourescence and/or TH immunohistochemistry. The score "1" is assigned to sections in which all neurons survive and are morphologically indistinguishable from non-lesioned neurons whereas the score "5" is assigned to sections in which no neurons survive in the 6-OHDA lesioned side.

The invention claimed:

1. A method of treatment or alleviation of Parkinson's disease in a subject, which method comprises administering to said subject a combination of at least one compound having a neurotrophic activity which mimics or enhances the function of NGF, BDNF, and/or GDNF and at least one compound having adenosine $A_{2A}$ receptor antagonist activity,
wherein the compound having a neurotrophic activity is at least one compound selected from the group consisting of: 5-(4-Chlorophenyl)-8-methyl-6,7,8,9-tetrahydro-1-H-pyrrolo[3.2-h]isoquinoline-2,3-dione-3-oxime; 5-(4-Chlorophenyl)-6,7,8,9-tetrahydro-1-H-pyrrolo[3.2-h]naphthalene-2,3-dione-3-oxime; GDNF; and neublastin; and pharmaceutically acceptable salts thereof; and the compound having adenosine $A_{2A}$ receptor antagonist activity is at least one compound selected from the group consisting of: KW-6002; ZM-241385; 8FB-PTP; SCH-58261; KF-17837; CGS-15943; DMPX; and pharmaceutically acceptable salts thereof, and
wherein the combination of compounds administered is effective for treating or alleviating Parkinson's disease.

2. The method according to claim 1, wherein the compound having a neurotrophic activity is GDNF and the compound having adenosine $A_{2A}$ antagonist activity is SCH-58261 or KF-17837.

3. A pharmaceutical composition comprising a therapeutically effective amount of at least one compound having a neurotrophic activity which mimics or enhances the function of NGF, BDNF, and/or GDNF and at least one compound having adenosine $A_{2A}$ receptor antagonist activity, wherein the compound having a neurotrophic activity is at least one compound selected from the group consisting of: 5-(4-Chlorophenyl)-8-methyl-6,7,8,9-tetrahydro-1-H-pyrrolo[3.2-h]isoquinoline-2,3-dione-3-oxime; 5-(4-chlorophenyl)-6,7,8,9-tetrahydro-1-H-pyrrolo[3.2-h]naphthalene-2,3-dione-3-oxime; GDNF; and neublastin; and pharmaceutically acceptable salts thereof; and the compound having adenosine $A_{2A}$ receptor antagonist activity is at least one compound selected from the group consisting of: KW-6002; ZM-241385; 8FB-PTP; SCH-58261; KF-17837; CGS-15943; DMPX; and pharmaceutically acceptable salts thereof, together with at least one pharmaceutically-acceptable carrier or diluent, wherein the therapeutically effective amount of the combination of compounds administered is an amount that is effective for treating or alleviating Parkinson's disease.

4. The pharmaceutical composition of claim 3, for use in the treatment or alleviation of Parkinson's disease in a subject.

5. A combination of at least one compound having a neurotrophic activity which mimics or enhances the function of NGF, BDNF, and/or GDNF and at least one compound having adenosine $A_{2A}$ receptor antagonist activity, wherein the compound having a neurotrophic activity is at least one compound selected from the group consisting of: 5-(4-chlorophenyl)-8-methyl-6,7,8,9-tetrahydro-1-H-pyrrolo[3.2-h]isoquinoline-2,3-dione-3-oxime; 5-(4-chlorophenyl)-6,7,8,9-tetrahydro-1-H-pyrrolo[3.2-h]naphthalene-2,3-dione-3-oxime; GDNF; and neublastin; and pharmaceutically acceptable salts thereof; and the compound having adenosine $A_{2A}$ receptor antagonist activity is at least one compound selected from the group consisting of: KW-6002; ZM-241385; 8FB-PTP; SCH-58261; KF-17837; CGS-15943; DMPX; and pharmaceutically acceptable salts thereof, for use as a therapeutic agent.

6. A kit of parts comprising at least one compound having a neurotrophic activity which mimics or enhances the function of NGF, BDNF, and/or GDNF and at least one compound having adenosine $A_{2A}$ receptor antagonist activity, wherein the compound having a neurotrophic activity is at least one compound selected from the group consisting of: 5-(4-chlorophenyl)-8-methyl-6,7,8,9-tetrahydro-1-H-pyrrolo[3.2-h]isoquinoline-2,3-dione-3-oxime; 5-(4-chlorophenyl)-6,7,8,9-tetrahydro-1-H-pyrrolo[3.2-h]naphthalene-2,3-dione-3-oxime; GDNF; and neublastin; and pharmaceutically acceptable salts thereof; and the compound having adenosine $A_{2A}$ receptor antagonist activity is at least one compound selected from the group consisting of: KW-6002; ZM-241385; 8FB-PTP; SCH-58261; KF-17837; CGS-15943; DMPX; and pharmaceutically acceptable salts thereof.

* * * * *